United States Patent
Narula et al.

(10) Patent No.: US 6,906,013 B1
(45) Date of Patent: Jun. 14, 2005

(54) CYCLOHEXANBUTANOL DERIVATIVE AND FRAGRANCE USE THEREOF

(75) Inventors: Anubhav P. S. Narula, Hazlet, NJ (US); Patrick M. Merritt, Ringoes, NJ (US); Richard Anthony Weiss, Livingston, NJ (US); Charles E. J. Beck, Summit, NJ (US)

(73) Assignee: International Flavors & Fragrances Inc., New York, NY (US)

( * ) Notice: Subject to any disclaimer, the term of this patent is extended or adjusted under 35 U.S.C. 154(b) by 5 days.

(21) Appl. No.: 10/873,566

(22) Filed: Jun. 22, 2004

(51) Int. Cl.[7] .............. C11D 3/50; A61K 7/46; C07C 35/14
(52) U.S. Cl. ............. 510/106; 512/22; 568/822
(58) Field of Search ............ 568/822; 510/106; 512/22

(56) References Cited

U.S. PATENT DOCUMENTS

| | | | |
|---|---|---|---|
| 2,947,780 | A | 8/1960 | Teegarden et al. |
| 4,534,891 | A | 8/1985 | Boden et al. |
| 6,632,788 | B2 | 10/2003 | Levorse, Jr. et al. |

FOREIGN PATENT DOCUMENTS

| | | | |
|---|---|---|---|
| DE | 29 38 689 A1 | | 9/1979 |
| EP | 0 025 939 | | 5/1982 |
| JP | 55-36461 | * | 3/1980 |

OTHER PUBLICATIONS

P. K. Grant et al., Australian Journal of Chemistry, vol. 44, 443–446, Mar., 1991.*

* cited by examiner

*Primary Examiner*—John R. Hardee
(74) *Attorney, Agent, or Firm*—Joseph F. Leightner; Alexander Migirov

(57) ABSTRACT

The novel compound, cyclohexanbutanol, 4-(hydroxymethyl)-alpha, alpha-dimethyl- having the structure:

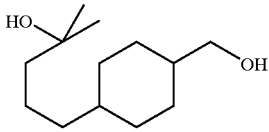

and the use of the compound in creating fragrances, and scents in items such as perfumes, colognes and personal care products is disclosed.

10 Claims, No Drawings

CYCLOHEXANBUTANOL DERIVATIVE AND FRAGRANCE USE THEREOF

FIELD OF THE INVENTION

The present invention relates to new chemical entities and the incorporation and use of the a novel compound and the use of this new molecule as fragrance chemicals.

BACKGROUND OF THE INVENTION

U.S. Pat. Nos. 2,947,780 and 6,632,788 among various other patents disclose cyclic chemicals that are suitable for use as fragrance chemicals. Those with skill in the art appreciate how differences in the chemical structure of the molecule can result in significant differences in the odor, notes and characteristics of a molecule. These variations and the ongoing need to discover and use the new chemicals in the development of new fragrances allow perfumers to apply the new compounds in creating new fragrances.

SUMMARY OF THE INVENTION

The present invention provides a novel molecule, and the use of the molecule to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the present invention is directed to the novel compound, cyclohexanbutanol, 4-hydroxymethyl)-alpha, alpha-dimethyl-, set forth below:

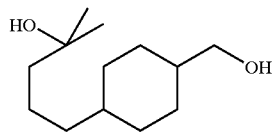

Another embodiment of the invention is a method for enhancing a fragrance by incorporating an olfactory acceptable amount of cyclohexanbutanol, 4-(hydroxymethyl)-alpha, alpha-dimethyl-. These and other embodiments of the present invention will be apparent by reading the following specification.

DETAILED DESCRIPTION OF THE INVENTION

The novel compound of the present invention can be prepared as described more completely in the examples that follow.

Cyclohexanbutanol, 4-(hydroxymethyl)-alpha, alpha-dimethyl-, has a fatty, floral, fresh fragrance, with green notes.

The use of the compound of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the fragranced article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

All U.S. patents and patent applications cited herein are incorporated by reference as if set forth in their entirety.

The following are provided as specific embodiments of the present invention. Other modifications of this invention will be readily apparent to those skilled in the art. Such modifications are understood to be within the scope of this invention. As used herein all percentages are weight percent unless otherwise noted, ml is understood to be milliliters, DPG is dipropylene glycol, g is understood to be grams. All of the fragrance ingredients used in the following examples are available from International Flavors & Fragrances Inc., Hazlet, N.J., U.S.A.

EXAMPLE 1

Preparation of Cyclohexanbutanol 4-(Hydroxymethyl)-Alpha, Alpha-Dimethyl- 1200 grams of LYRAL (IFF) was fed into an 18 inch column that contained palladium and $Al_2O_3$ (18 grams).

Isopropyl alcohol (260 grams) was fed to the column as well as hydrogen at a temperature of 120° C. and 600 pounds per square inch.

The reaction was allowed to run for approximately 27 hours.

The NMR data for the resulting product was the following:

1.2 ppm (s,6H), 1.23–1.8 ppm (m, 14H), 1.97 ppm (bs, 1H), 2.5 ppm (bs, 1H), 3.48 ppm (d, 2H)

EXAMPLE 2

Use of the Compound in a Fragrance

A fragrance was prepared according to the following formulation, all weights are in grams:

| DESCRIPTION | QUANTITY |
| --- | --- |
| Ambrettolide | 2.00 |
| Hedione | 2.00 |
| Helional | 0.20 |
| Hexyl Cinnamic Aldehyde | 9.00 |
| Cyclohexanbutanol, 4-(Hydroxymethyl)-Alpha, Alpha-Dimethyl- | 20.00 |
| Indolarome 10% DPG | 0.40 |
| Iso E Super | 4.00 |
| Meijiff | 40.00 |
| Montaverdi | 0.40 |
| Phenyl Ethyl Alcohol | 12.00 |
| Phenoxanol | 9.00 |
| Terpineol Coeur | 1.00 |

This fragrance was described as having a floral note which was enhanced by the incorporation of the cyclohexanbutanol, 4-hydroxymethyl)-alpha, alpha-dimethyl-.

What is claimed is:

1. The compound cyclohexanbutanol, 4-(hydroxymethyl)-alpha, alpha-dimethyl-.

2. A fragrance formulation containing an olfactory effective amount of the compound of claim 1.

3. A composition comprising an olfactory acceptable amount of the compound of claim 1 in a product selected from perfumes, colognes, toilet waters, personal care products, cleaning products and air fresheners.

4. A method for improving, enhancing or modifying the odor properties of a fragrance by incorporating an olfactory acceptable amount of the compound of claim 1.

5. The method of claim 4 wherein the fragrance is incorporated into a product selected from perfumes, colognes, toilet waters, personal care products, cleaning products and air fresheners.

6. The method of claim 5 wherein the cleaning product is selected from the group consisting of detergents, dishwashing compositions, scrubbing compounds and window cleaners.

7. The method of claim 6 wherein the product is a personal care product.

8. A method for improving, enhancing or modifying the odor properties of a fragrance by incorporating an olfactory acceptable amount of the compound of claim 1.

9. The method of claim 8 wherein the compound is incorporated at a level of from about 0.005 to about 10 weight percent.

10. The method of claim 8 wherein compound is incorporated at a level of from about 0.5 to about 8 weight percent.

* * * * *